US008017139B2

(12) United States Patent
Thomas et al.

(10) Patent No.: US 8,017,139 B2
(45) Date of Patent: Sep. 13, 2011

(54) BLEND HYDROGELS AND METHODS OF MAKING

(75) Inventors: Brian Thomas, Columbia City, IN (US); Donald Yakimicki, Plymouth, IN (US); Robert Garryl Hudgins, Burnsville, MN (US)

(73) Assignee: Zimmer Technology, Inc., Warsaw, IN (US)

( * ) Notice: Subject to any disclaimer, the term of this patent is extended or adjusted under 35 U.S.C. 154(b) by 1075 days.

(21) Appl. No.: 11/358,383

(22) Filed: Feb. 21, 2006

(65) Prior Publication Data

US 2006/0188487 A1    Aug. 24, 2006

Related U.S. Application Data

(60) Provisional application No. 60/656,453, filed on Feb. 23, 2005.

(51) Int. Cl.
  *A61F 13/00* (2006.01)
(52) U.S. Cl. .................................................. 424/422
(58) Field of Classification Search .................. None
  See application file for complete search history.

(56) References Cited

U.S. PATENT DOCUMENTS

| | | |
|---|---|---|
| 3,200,178 A | 8/1965 | Kanji |
| 3,862,265 A | 1/1975 | Steinkamp et al. |
| 3,875,302 A | 4/1975 | Inoue |
| 4,036,788 A | 7/1977 | Steckler |
| 4,058,491 A | 11/1977 | Steckler |
| 4,060,678 A | 11/1977 | Steckler |
| 4,071,508 A | 1/1978 | Steckler |
| 4,279,795 A | 7/1981 | Yamashita et al. |
| 4,300,820 A | 11/1981 | Shah |
| 4,379,874 A | 4/1983 | Stoy |
| 4,451,599 A * | 5/1984 | Odorzynski et al. .......... 524/169 |
| 4,451,630 A | 5/1984 | Atkinson et al. |
| 4,464,438 A * | 8/1984 | Lu ................................. 428/516 |
| 4,472,542 A | 9/1984 | Nambu |
| 4,640,941 A | 2/1987 | Park et al. |
| 4,656,216 A | 4/1987 | Muller et al. |
| 4,663,358 A | 5/1987 | Hyon et al. |
| 4,664,857 A | 5/1987 | Nambu |
| 4,699,146 A | 10/1987 | Sieverding |
| 4,734,097 A | 3/1988 | Tanabe et al. |
| 4,771,089 A | 9/1988 | Ofstead |
| 4,772,287 A | 9/1988 | Ray et al. |
| 4,808,353 A | 2/1989 | Nambu et al. |
| 4,842,597 A | 6/1989 | Brook |
| 4,851,168 A | 7/1989 | Graiver et al. |
| 4,859,719 A | 8/1989 | Ofstead |
| 4,871,490 A | 10/1989 | Rosiak et al. |
| 4,874,562 A | 10/1989 | Hyon et al. |
| 4,915,974 A | 4/1990 | D'Amelia et al. |
| 4,956,122 A | 9/1990 | Watts et al. |
| 4,966,924 A | 10/1990 | Hyon et al. |
| 4,988,761 A | 1/1991 | Ikada et al. |
| 5,028,648 A | 7/1991 | Famili et al. |
| 5,047,055 A | 9/1991 | Bao et al. |
| 5,053,455 A | 10/1991 | Kroggel et al. |
| 5,106,876 A | 4/1992 | Kawamura |
| 5,118,779 A | 6/1992 | Szycher |
| 5,122,565 A | 6/1992 | George |
| 5,157,093 A | 10/1992 | Harisiades et al. |
| 5,189,097 A | 2/1993 | LaFleur et al. |
| 5,192,326 A | 3/1993 | Bao et al. |
| 5,244,799 A | 9/1993 | Anderson |
| 5,276,079 A | 1/1994 | Duan et al. |
| 5,288,503 A | 2/1994 | Wood et al. |
| 5,306,311 A | 4/1994 | Stone et al. |
| 5,311,223 A | 5/1994 | Vanderlaan |
| 5,315,478 A | 5/1994 | Cadwell et al. |
| 5,334,634 A * | 8/1994 | Bastiolo et al. ................. 524/47 |
| 5,336,551 A | 8/1994 | Graiver et al. |
| 5,358,525 A | 10/1994 | Fox et al. |
| 5,360,830 A * | 11/1994 | Bastioli et al. ............... 521/84.1 |
| 5,362,803 A | 11/1994 | LaFleur et al. |
| 5,364,547 A | 11/1994 | Babb et al. |
| 5,407,055 A | 4/1995 | Tanaka |
| 5,409,966 A | 4/1995 | Duan et al. |
| 5,410,016 A | 4/1995 | Hubbell et al. |
| 5,458,643 A | 10/1995 | Oka et al. |
| 5,527,271 A | 6/1996 | Shah et al. |

(Continued)

FOREIGN PATENT DOCUMENTS

EP    0256293    2/1988

(Continued)

OTHER PUBLICATIONS

Bryant, Stephanie J. et al., "Crosslinking Density Influences Chondrocyte Metabolism in Dynamically Leaded Photocrosslinked Poly(ethylene glycol) Hydrogels", *Annals of Biomedical Engineering*, Mar. 2004, pp. 407-417, vol. 3, No. 3, Biomedical Engineering Society.

Bryant, Stephanie J. et al., "The effects of scaffold thickness on tissue engineered cartilage in photocrosslinked poly(ethylene oxide) hydrogels", *Biomaterials* 22, 2001, pp. 619-626, Elsevier Science Ltd.

Bryant, Stephanie J. et al., "Photocrosslinkable Poly(ethylene oxide) and Poly(vinyl alcohol) Hydrogels for Tissue Engineering Cartilage", 21st Annual Conference and the 1999 Annual Fall Meeting of the Biomedical Engineering Society, Oct. 13-16, 1999, Atlanta, GA, USA; *Engineering in Medicine and Biology* 1999, p. 751, vol. 2, IEEE.

(Continued)

*Primary Examiner* — Michael G Hartley
*Assistant Examiner* — Paul Dickinson
(74) *Attorney, Agent, or Firm* — Cook Alex Ltd.

(57) ABSTRACT

The present invention provides blend water-swellable materials and hydrogels suitable for use in biomedical or other applications. The blend water swellable materials and hydrogels have at least one hydrophilic polymer and at least one other polymer or oligomer having both hydrophobic and hydrophilic recurring units where the blend phase separates and is opaque and immiscible in the presence of water. Methods of making these blend water-swellable materials and hydrogels are also described.

14 Claims, 1 Drawing Sheet

U.S. PATENT DOCUMENTS

| | | | |
|---|---|---|---|
| 5,540,033 | A | 7/1996 | Fox et al. |
| 5,552,096 | A | 9/1996 | Auda et al. |
| 5,576,072 | A | 11/1996 | Hostettler et al. |
| 5,580,938 | A | 12/1996 | Gutweiler et al. |
| 5,624,463 | A | 4/1997 | Stone et al. |
| 5,632,774 | A | 5/1997 | Babian |
| 5,674,295 | A | 10/1997 | Ray et al. |
| 5,681,300 | A | 10/1997 | Ahr et al. |
| 5,705,296 | A | 1/1998 | Kamauchi et al. |
| 5,709,854 | A | 1/1998 | Griffith-Cima et al. |
| 5,711,960 | A | 1/1998 | Shikinami |
| 5,716,404 | A | 2/1998 | Vacanti et al. |
| 5,723,331 | A | 3/1998 | Tubo et al. |
| 5,834,029 | A | 11/1998 | Bellamkonda et al. |
| 5,879,713 | A | 3/1999 | Roth et al. |
| 5,891,826 | A | 4/1999 | Tsaur et al. |
| 5,941,909 | A | 8/1999 | Purkait |
| 5,976,186 | A | 11/1999 | Bao et al. |
| 5,981,826 | A | 11/1999 | Ku et al. |
| 6,015,576 | A | 1/2000 | See et al. |
| 6,017,577 | A | 1/2000 | Hostettler et al. |
| 6,040,493 | A | 3/2000 | Cooke et al. |
| 6,080,488 | A | 6/2000 | Hostettler et al. |
| 6,117,449 | A | 9/2000 | See et al. |
| 6,120,904 | A | 9/2000 | Hostettler et al. |
| 6,121,341 | A | 9/2000 | Sawhney et al. |
| 6,129,761 | A | 10/2000 | Hubbell |
| 6,132,468 | A | 10/2000 | Mansmann |
| 6,139,963 | A | 10/2000 | Fujii et al. |
| 6,146,686 | A | 11/2000 | Leitao |
| 6,156,345 | A | 12/2000 | Chudzik et al. |
| 6,156,572 | A | 12/2000 | Bellamkonda et al. |
| 6,162,456 | A | 12/2000 | Dunbar et al. |
| 6,180,132 | B1 | 1/2001 | Huang et al. |
| 6,180,606 | B1 | 1/2001 | Chen et al. |
| 6,184,197 | B1 | 2/2001 | Heinzman et al. |
| 6,187,048 | B1 | 2/2001 | Milner et al. |
| 6,207,185 | B1 | 3/2001 | See et al. |
| 6,211,296 | B1 | 4/2001 | Frate et al. |
| 6,224,893 | B1 | 5/2001 | Langer et al. |
| 6,231,605 | B1 | 5/2001 | Ku |
| 6,232,406 | B1 | 5/2001 | Stoy |
| 6,238,691 | B1 | 5/2001 | Huang |
| 6,268,405 | B1 | 7/2001 | Yao et al. |
| 6,271,278 | B1 | 8/2001 | Park et al. |
| 6,280,475 | B1 | 8/2001 | Bao et al. |
| 6,306,424 | B1 | 10/2001 | Vyakarnam et al. |
| 6,365,149 | B2 | 4/2002 | Vyakarnam et al. |
| 6,371,984 | B1 | 4/2002 | Van Dyke et al. |
| 6,372,283 | B1 | 4/2002 | Shim et al. |
| 6,375,634 | B1 | 4/2002 | Carroll |
| 6,387,325 | B1 | 5/2002 | Keusch et al. |
| 6,402,784 | B1 | 6/2002 | Wardlaw |
| 6,443,988 | B2 | 9/2002 | Felt et al. |
| 6,509,098 | B1 | 1/2003 | Merrill et al. |
| 6,531,147 | B2 | 3/2003 | Sawhney et al. |
| 6,533,817 | B1 | 3/2003 | Norton et al. |
| 6,583,219 | B2 | 6/2003 | Won et al. |
| 6,602,952 | B1 | 8/2003 | Bentley et al. |
| 6,608,117 | B1 | 8/2003 | Gvozdic |
| 6,620,196 | B1 | 9/2003 | Trieu |
| 6,626,945 | B2 | 9/2003 | Simon et al. |
| 6,629,997 | B2 | 10/2003 | Mansmann |
| 6,630,457 | B1 | 10/2003 | Aeschlimann et al. |
| 6,632,246 | B1 | 10/2003 | Simon et al. |
| 6,645,517 | B2 | 11/2003 | West et al. |
| 6,692,738 | B2 | 2/2004 | MacLaughlin et al. |
| 6,706,690 | B2 | 3/2004 | Reich et al. |
| 6,709,668 | B2 | 3/2004 | Won et al. |
| 6,710,104 | B2 | 3/2004 | Haraguchi |
| 6,710,126 | B1 | 3/2004 | Hirt et al. |
| 6,723,781 | B1 | 4/2004 | Frate et al. |
| 6,730,298 | B2 | 5/2004 | Griffith-Cima et al. |
| 6,733,533 | B1 | 5/2004 | Lozier |
| 6,780,840 | B1 | 8/2004 | DeVore et al. |
| 6,783,546 | B2 | 8/2004 | Zucherman et al. |
| 6,783,721 | B2 | 8/2004 | Higham et al. |
| 6,803,420 | B2 | 10/2004 | Cleary et al. |
| 6,852,772 | B2 | 2/2005 | Muratogulu et al. |
| 6,855,743 | B1 | 2/2005 | Gvozdic |
| 6,861,067 | B2 | 3/2005 | McGhee et al. |
| 7,235,592 | B2 | 6/2007 | Muratoglu et al. |
| 7,531,000 | B2 | 5/2009 | Hodorek |
| 2001/0026810 | A1 | 10/2001 | McGhee et al. |
| 2001/0032019 | A1 | 10/2001 | Van Dyke et al. |
| 2001/0049417 | A1 | 12/2001 | Frate et al. |
| 2001/0053897 | A1 | 12/2001 | Frate et al. |
| 2002/0022884 | A1 | 2/2002 | Mansmann |
| 2002/0026244 | A1 | 2/2002 | Trieu |
| 2002/0029083 | A1 | 3/2002 | Zucherman et al. |
| 2002/0049498 | A1 | 4/2002 | Yuksel et al. |
| 2002/0131952 | A1 | 9/2002 | Hennink et al. |
| 2002/0151979 | A1 | 10/2002 | Lambrecht et al. |
| 2002/0173855 | A1 | 11/2002 | Mansmann |
| 2002/0193531 | A1 | 12/2002 | Stoy et al. |
| 2003/0008396 | A1 | 1/2003 | Ku |
| 2003/0065389 | A1 | 4/2003 | Petersen |
| 2003/0080465 | A1 | 5/2003 | Higham et al. |
| 2003/0099709 | A1 | 5/2003 | Shah et al. |
| 2003/0130427 | A1 | 7/2003 | Cleary et al. |
| 2003/0152528 | A1 | 8/2003 | Singh et al. |
| 2003/0170308 | A1 | 9/2003 | Cleary et al. |
| 2003/0195628 | A1 | 10/2003 | Bao et al. |
| 2003/0232895 | A1 | 12/2003 | Omidian et al. |
| 2003/0236323 | A1 | 12/2003 | Ratner et al. |
| 2004/0002764 | A1 | 1/2004 | Gainor et al. |
| 2004/0005423 | A1 | 1/2004 | Dalton et al. |
| 2004/0030392 | A1 | 2/2004 | Lambrecht et al. |
| 2004/0039447 | A1 | 2/2004 | Simon et al. |
| 2004/0092653 | A1 | 5/2004 | Ruberti et al. |
| 2004/0096509 | A1 | 5/2004 | Hutchens et al. |
| 2004/0116641 | A1 | 6/2004 | Mather et al. |
| 2004/0121951 | A1 | 6/2004 | Rhee |
| 2004/0127618 | A1 | 7/2004 | Ulmer |
| 2004/0127992 | A1 | 7/2004 | Serhan et al. |
| 2004/0131582 | A1 | 7/2004 | Grinstaff et al. |
| 2004/0133280 | A1 | 7/2004 | Trieu |
| 2004/0143329 | A1 | 7/2004 | Ku |
| 2004/0147673 | A1 | 7/2004 | Calabro et al. |
| 2004/0153163 | A1 | 8/2004 | Posner |
| 2004/0161444 | A1 | 8/2004 | Song et al. |
| 2004/0171740 | A1 | 9/2004 | Ruberti et al. |
| 2004/0199250 | A1 | 10/2004 | Fell |
| 2004/0220296 | A1 | 11/2004 | Lowman et al. |
| 2004/0242770 | A1 | 12/2004 | Feldstein et al. |
| 2004/0244978 | A1 | 12/2004 | Shaarpour |
| 2005/0004560 | A1 | 1/2005 | Cox |
| 2005/0027069 | A1 | 2/2005 | Rhee et al. |
| 2005/0048103 | A1 | 3/2005 | Cleary et al. |
| 2005/0049365 | A1 | 3/2005 | Cleary et al. |
| 2005/0075454 | A1 | 4/2005 | Plochocka et al. |
| 2005/0095296 | A1 | 5/2005 | Lowman et al. |
| 2005/0107561 | A1 | 5/2005 | Lee et al. |
| 2005/0197441 | A1 | 9/2005 | Shibutani |
| 2006/0078587 | A1 | 4/2006 | Leong |
| 2006/0141002 | A1 | 6/2006 | Liu et al. |
| 2006/0188487 | A1 | 8/2006 | Thomas et al. |
| 2007/0004861 | A1 | 1/2007 | Cai |
| 2007/0202323 | A1 | 8/2007 | Kleiner et al. |
| 2007/0293651 | A1 | 12/2007 | Teda |
| 2008/0090145 | A1 | 4/2008 | Hiwara |
| 2009/0053318 | A1 | 2/2009 | Tan et al. |

FOREIGN PATENT DOCUMENTS

| | | |
|---|---|---|
| EP | 0 290 616 | 11/1988 |
| EP | 0 365 108 | 4/1990 |
| EP | 0 505 634 | 9/1992 |
| EP | 0 696 210 | 2/1996 |
| EP | 738762 A1 | 4/1996 |
| EP | 0 784 987 | 7/1997 |
| EP | 0 835 143 | 4/1998 |
| EP | 0 845 480 | 6/1998 |
| EP | 0 927 053 | 7/1999 |
| EP | 1 079 224 | 2/2001 |
| EP | 1 174 463 | 1/2002 |
| EP | 1593400 | 11/2005 |
| EP | 1595899 | 11/2005 |

| | | |
|---|---|---|
| FR | 2786400 | 6/2000 |
| FR | 2865939 | 8/2005 |
| FR | 2866571 | 8/2005 |
| GB | 2338958 | 10/2000 |
| JP | 01178545 | 7/1987 |
| JP | 01-305959 | 12/1989 |
| JP | 03-141957 | 6/1991 |
| JP | 04-303444 | 10/1992 |
| JP | 09-124730 | 5/1997 |
| JP | 09-124731 | 5/1997 |
| JP | 10-036534 | 2/1998 |
| JP | 10-043286 | 2/1998 |
| JP | 10036534 | 2/1998 |
| WO | WO 90/15082 | 12/1990 |
| WO | WO 94/13235 | 6/1994 |
| WO | WO 94/17851 | 8/1994 |
| WO | WO 95/02616 | 1/1995 |
| WO | WO 95/26699 | 10/1995 |
| WO | WO 98/17215 | 4/1998 |
| WO | WO 98/53768 | 12/1998 |
| WO | WO 99/03454 | 1/1999 |
| WO | WO 99/13923 | 3/1999 |
| WO | WO 99/67320 | 12/1999 |
| WO | WO 01/17574 | 3/2001 |
| WO | WO 01/19283 | 3/2001 |
| WO | WO 01/77197 | 10/2001 |
| WO | WO 02/04570 | 1/2002 |
| WO | WO 02/13871 | 2/2002 |
| WO | WO 02/060501 | 8/2002 |
| WO | WO 02/087642 | 11/2002 |
| WO | WO 02/087645 | 11/2002 |
| WO | WO 03/008007 | 1/2003 |
| WO | WO 03/074099 | 9/2003 |
| WO | WO 03/082359 | 10/2003 |
| WO | WO 2004/007651 | 1/2004 |
| WO | WO 2004/029174 | 4/2004 |
| WO | WO 2004/031253 | 4/2004 |
| WO | WO 2004/047690 | 6/2004 |
| WO | WO 2004/055057 | 7/2004 |
| WO | WO 2004/060427 | 7/2004 |
| WO | WO 2004/063388 | 7/2004 |
| WO | WO 2004/064693 | 8/2004 |
| WO | WO 2004/066704 | 8/2004 |
| WO | WO 2004/069296 | 8/2004 |
| WO | WO 2004/072138 | 8/2004 |
| WO | WO 2004/093786 | 11/2004 |
| WO | WO 2005/004943 | 1/2005 |
| WO | WO 2005/030832 | 4/2005 |
| WO | WO 2005/035726 | 4/2005 |
| WO | WO 2006/021054 | 3/2006 |
| WO | WO 2006/091706 | 8/2006 |
| WO | WO 2007/067697 | 6/2007 |
| WO | WO 2007/015208 | 8/2007 |
| WO | WO 2008/144514 | 11/2008 |
| WO | WO 2009/020793 | 2/2009 |
| WO | WO 2009/032430 | 3/2009 |
| WO | WO 2009/088654 | 5/2010 |

OTHER PUBLICATIONS

Durmaz, S. et al., "Phase separation during the formation of poly(acrylamide) hydrogels", *Polymer* 41, 2000, pp. 5729-5735, Elsevier Science Ltd.

Gong, J.P. et al., "Friction of Polymer Gels and the Potential Application as Artificial Cartilage", *SPIE*, Mar. 1999, pp. 218-225, vol. 3669.

Guilherme, R. et al., "Hydrogels based on PAAm network with PNIPAAm included: hydrophilic—hydrophobic transition measured by the partition of Orange II and Methylene Blue in water", *Polymer* 44, 2003, pp. 4213-4219, Elsevier Science Ltd.

Hassan, Christie M. et al., "Cellular PVA Hydrogels Produced by Freeze/Thawing", *J Appl Polym Sci*, 2000, pp. 2075-2079, vol. 76, John Wiley & Sons, Inc.

Hassan, Christie M. et al., "Diffusional characteristics of freeze/thawed poly(vinyl alcohol) hydrogels: Applications to protein controlled release from multilaminate devices", *European Journal of Pharmaceuticals and Biopharmaceutics* 49, 2000, pp. 161-165, Elsevier Science B.V.

Hassan, C.M. et al., "Modeling of crystal dissolution of poly(vinyl alcohol) gels produced by freezing/thawing processes", *Polymer* 41, 2000, pp. 6729-6739, Elsevier Science Ltd.

Hassan, Christie M. et al., "Structure and Applications of Poly(vinyl alcohol) Hydrogels Produced by Conventional Crosslinking or by Freezing/Thawing Methods", *Polymer Science*, 2000, pp. 37-65, vol. 153, Springer-Verlag Berlin Heidelberg.

Hassan, Christie M. et al., "Structure and Morphology of Freeze/Thawed PVA Hydrogels", *Macromolecules*, 2000, pp. 2472-2479, vol. 33, No. 7, American Chemical Society.

Hickey, Alla S. et al., "Mesh size and diffusive characteristics of semicrystalline poly(vinyl alcohol) membranes prepared by freezing/thawing techniques", *Journal of Membrane Science* 107, 1995, pp. 229-237, Elsevier Science B.V.

Hickey, Alla S. et al., "Solute diffusion in poly(vinyl alcohol) / poly(acrylic acid) composite membranes prepared by freezing/thawing techniques", *Polymer*, 1997, pp. 5931-5936, vol. 38, No. 24, Elsevier Science Ltd., printed in Great Britain.

Jenkins, A.D. et al., "Glossary of Basic Terms in Polymer Science", International Union of Pure and Applied Chemistry (IUPAC) Recommendations 1996, *Pure & Appl Chem*, 1996, pp. 2287-2311, vol. 68, No. 12, IUPAC, printed in Great Britain.

Kobayashi, Masanori et al., "Development of an artificial meniscus using polyvinyl alcohol-hydrogel for early return to, and continuance of, athletic life in sportspersons with severe meniscus injury. II: Animal experiments" Abstract Only, *The Knee* 10, 2003, p. 53, Elsevier Science B.V.

Kobayashi, Masanori et al., "Preliminary study of polyvinyl alcohol-hydrogel (PVA-H) artificial meniscus", *Biomaterials* 24, 2003, pp. 639-647, Elsevier Science Ltd.

Lester, Christopher L. et al., "Physical Properties of Hydrogels Synthesized from Lyotropic Liquid Crystalline Templates", *Chem Mater* 15, 2003, pp. 3376-3384, American Chemical Society.

Mano, Valdir et al., "Blends Composed of Poly(N-isopropylacrylamide) and an EthyleneNinyl Alcohol Copolymer: Thermal and Morphological Studies", *Journal of Applied Polymer Science*, 2004, pp. 501-505, vol. 91, Wiley Periodicals, Inc.

Noguchi, Takashi et al., "Poly(vinyl Alcohol) Hydrogel As an Artificial Articular Cartilage:. Evaluation of Biocompatibility", *Journal of Applied Biomaterials*, 1991, pp. 101-107, vol. 2, John Wiley & Sons, Inc.

Oka, M. et al., "Development of artificial articular cartilage", *Proc Instn Mech Engrs*, 2000, pp. 59-68, vol. 214, Part H, IMechE.

Park, Jae Hyung et al., "Hydrogels based on poly(ethylene oxide) and poly(tetramethylene oxide) or poly(dimethyl siloxane). III. In vivo biocompatibility and biostability", *J Biomed Mater Res* 64A, 2003, pp. 309-319, Wiley Periodicals, Inc.

Peppas, N. A. et al., "Physicochemical Foundations and Structural Design of Hydrogels in Medicine and Biology", *Annu Rev Biomed Eng*, 2000, pp. 9-29, vol. 2, Annual Reviews.

Schmedlen, Rachael H. et al., "Photocrosslinkable polyvinyl alcohol hydrogels that can be modified with cell adhesion peptides for use in tissue engineering", *Biomaterials* 23, 2002, pp. 4325-4332, Elsevier Science Ltd.

Suggs, Laura J. et al., "In vitro cytotoxicity and in vivo biocompatibility of poly(propylene fumarate-co-ethylene glycol) hydrogels", *J Biomed Mater Res*, 1999, pp. 22-32, vol. 46, John Wiley & Sons, Inc.

Thomas, Jonathan D., "Novel Associated PVA/PVP Hydrogels for Nucleus Pulposus Replacement", Thesis, Master of Science in Materials Engineering Degree, Drexel University, Sep. 2001, 60 pgs.

Ushio, Kazuyasu et al., "Attachment of Artificial Cartilage to Underlying Bone", *J Biomed Mater Res Part B: Appl Biomater* 68B, 2004, pp. 59-68, Wiley Periodicals, Inc.

Ushio, K. et al., "Partial hemiarthroplasty for the treatment of osteonecrosis of the femoral head: An Experimental Study in the Dog", *J Bone Joint Surg [Br]*, 2003, pp. 922-930, vol. 85-B, British Editorial Society of Bone and Joint Surgery.

Zhang, Xianzheng et al., "Synthesis and characterization of partially biodegradable, temperature and pH sensitive DEX-MA/PNIPAAm hydrogels", *Biomaterials* 25, 2004, pp. 4719-4730, Elsevier Ltd.

"Lecture 7: Hydrogel Biomaterials: Structure and Physical Chemistry", Spring 2003, 8 pgs.

European Patent Office, Search Report and Written Opinion for corresponding PCT Application No. PCT/US2006/006356, Jun. 22, 2006, 9 pp.

Anseth, Kristi, et al., "In situ Forming degradable networks and their applications in tissue engineering and drug delivery", Journal of Controlled Release, vol. 78, pp. 199-209, 2002.

Babb. David, et al, "Perfluorcyclobutane Aromatic Ether Polymers. III. Synthesis and Thermal Stability of a Thermoset Polymer containing Triphenylphosphine Oxide", Journal of Applied Polymer Science, vol. 69, pp. 2005-2012, 1998.

Bass, Lawrence, et al., "Laser Tissue Welding: A comprehensive Review of Current and Future Clinic Applications", Lasers in Surgery and Medicine, vol. 17, pp. 315-349, 1995.

Bray, James, et al, "Poly(vinyl Alcohol) Hydrogels. Formation by Electron Beam Irradiation of Aqueous Solutions and Subsequent Crystallization," Journal of Applied Polymer Science, vol. 17, pp. 3779-3794, 1973.

Bray, James, et al. "Poly(vinyl alcohol) Hydrogels for synthetic Articular Cartilage Material," Biomed Material Review, vol. 7, pp. 431-443, 1973.

Carey et al., Adv. Org. Chem., Part B., p. 829, 2001.

Chow et al. "Octacalcium Phosphate," Monograph in Oral Science, vol. 18, pp. 94-111 and 130-147, 2001.

Covert, Rebeccah, et al., "Friction & Wear Testing of new Biomaterial for use as an Articular Cartilage Substitute", Bioengineering Conference, ASME 2001 pp. 355-356.

Ding, Mei Yee , "Characterisation of Poly vinyl-alcohol Hydrogels" May 17, 2003.

Green, Mark, et al., Organic Chemistry Principles and Industrial Practice, Wiley VCH, 2003.

Haralabakopoulus, A. et al., "Modification of Poly(vinyl alcohol) Polymers by Aliphatic Carboxylic Acids via Reactive Blending," Journal of Applied Polymer Science, vol. 69, pp. 1885-1890, 1998.

Hickey et al., "Mesh Size and Diffusive Characteristics Of Semicrystalline . . . ", Journal of Membrane Science 107 (1995) pp. 229-237.

Jagur-Grodzinski, Joseph, "Biomedical application of functional polymers" Reactive & Functional Polymers, vol. 39 pp. 99-138, 1999.

Kawanishi, Kazuo, et al. "Thermodynamic consideration of the sol-gel transition in polymer solutions", 35th Annual Mtgof the Society of Polymer Science, Japan 1986.

LeGeros R. Z., "Calcium Phosphates In Oral Biology and Medicine," Monograph in Oral Science, vol. 15, pp. 1-201, 1991.

Li, Bin, et al, "Synthesis of a Self-Gelatinizable Grafting Copolymer of Poly(vinyl Alcohol) for construction of an Amperometric Peroxidase Electrode," Analytical Biochemistry, vol. 256, pp. 130-132, 1998.

Lin-Gibson, Sheng, et al, "Synthesis and Characterization of PEG Dimethacrylates and Their Hydrogels" Biomacromolecules, vol. 5, pp. 1280-1287, 2004.

Lozinsky, Vladimir, et al, "Study of Cryostructuration of Polymer Systems. XIV. Poly(vinyl alcohol) Cryogels: Apparent Yield of the Freeze-Thaw-Induced Gelation of Concentrated Aqueous Solutions of the Polymer". Journal of Applied Polymer Sc., p. 1822-1831 2000.

Lozinsky, Vladimer,. at al. "Study of Cryostructuration of Polymer Systems. XVII. Poly(vinyl alcohol) Cryogels:Dynamics of the Cryotropic Gel Formation," Journal of Applied Polymer Science, vol. 77, pp. 2017-2023, 2000.

Lozinsky, Vladimer, at al., "On the Possibility of Mechanodestruction of Poly(vinyl alcohol) molecules under Moderate Freezing of its Concentrated Water Solution" Polymer Bulletin, vol. 15, pp. 333-340, 1986.

Lozinsky, Vladimer, et al, "Swelling behavior of poly9vinyl alcohol) cryogels employed as matrices for cell immobilization", Enzyme Microb. Technology, vol. 18, pp. 561-569. 1996.

Lu. Sanxiu, et al., "Photopolymerization of multilaminated poly(HEMA) hydrogels for controlled release," Journal of Controlled Release, vol. 57, pp. 291-300, 1999.

Mondino, A.V., et al, "Physical properties of gamma irradiated poly(vinyl alcohol) hydrogel preparations", Radiation Physics and Chemistry, vol. 55, pp. 723-726, 1999.

Moro, Toru, et al, "Surface Grafting of artifical joints with a biocompatible polymer for preventing periprosthetic osteolysis", Nature Materials, vol. 3, pp. 829-836, 2004.

Park, Kyoung Ran, et al, "Synthesis of PVA/PVP hydrogels having two-layer by radiation and their physical properties," Radiation Physics and Chemistry, vol. 67, pp. 361-365, 2003.

Peppas, Nikolaos, et al., "Reinforced uncrosslinked poly(vinyl-alcohol) gels produced by cyclic freezing-thawing processes: a short review", Journal of Controlled Release, vol. 16 pp. 305-310, 1991.

Rao, Linfeng, et al, "Complexation of Eu(III) with alkyl-substituted malonamides in acetonitrile," Journal of Chemical Society, pp. 1939-1944, 2001.

Rosiak, J.M., et al., "Synthesis of Hydrogels by irradiation of polymers in aqueous solution" Radiation Physics and Chemistry, vol. 55, pp. 139-151, 1999.

Stammen, J.A., et al, "Mechanical properties of a novel PVA hydrogel in shear and unconfined compression", Biomaterials, pp. 799-806 abstract only, 2001.

Taguchi, Tetsushi, et al, "Hydroxyapatite Formation on/in Poly(vinyl alcohol) Hydrogel Matrices Using a Novel Alternate Soaking Process," Chemistry Letters, pp. 711-712, 1998.

Tripathy, T., at al., "Novel Flocculating agent based on sodium alginate and acrylamide", European Polymer Journal, vol. 35, pp. 2057-2072, 1999.

Ulanski, Piotr, et al., "OH-radical-induced crosslinking and strand breakage of poly(vinyl alcohol) in aqueous solution in the absence and presence of oxygen. A pulse radiolysis and product study", Macromol. Chem. Phys., vol. 195, pp. 1443-1461, 1994.

Urushizaki, Fumio, et al, "Swelling & Mechanical properties of poly(vinyl alcohol) hydrogels" International Journal of Pharmaceutics, vol. 58, pp. 135-142, 1990.

Wang, Benlian, et al, "The influence of polymer concentration on the radiation-chemical yield of intermolecular crosslinking of poly(vinyl alcohol) by y-rays in deoxygenated aqueous solution", Radiation Physics and Chemistry, vol. 59 pp. 91-95, 2000.

West, Jennifer, et al, "Photopolymerized hydrogel materials for drug delivery applications," Reactive Polymers, vol. 25, pp. 139-147, 1995.

Yamaura, Kazuo, at al, "Properties of Gels Obtained by Freezing/Thawing of Poly(vinyl Alcohol)/Water/Dimethyl Sulfoxide Solutions," Journal of Applied Polymer Science, vol. 37 pp. 2709-2718, 1989.

Yokoyama, F., et al, "Morphology & Structure of highly elastic poly (vinyl alcohol) hydrogel prepared by repeated freezing-and-melting," Colloid & Polymer Science, vol. 264, pp. 595-601, 1986.

EP Search Report for EP Application No. 05001009 9-2115 dated Mar. 1, 2005.

Search Report and Written Opinion for PCT/US2006/006356 dated Jun. 22, 2006, 9 pgs.

EP Search Report for EP 06256525.4 dated May 10, 2007.

EP Search Report for EP 06256452.1 dated May 23, 2007.

Search Report and Written Opinion for PCT/US2006/046725 dated Jul. 28, 2008, 20 pgs.

Preliminary Examination Report and Search Report for PCT/EP2005/010931 dated Feb. 6, 2007.

Search Report and Written Opinion for PCT/US2007/064782 dated May 30, 2008.

Search Report and Written Opinion for PCTUS2008071435 dated Feb. 5, 2009.

EPO Invitation to Pay additional fees and Annex to Search Report for PCT/US2006/046725 dated Apr. 22, 2008, 8 pages.

Search Report and Written Opinion for PCT/US2008/071435 dated Feb. 5, 2009.

Preliminary Report on Patentability & Written Opinion for PCT/US2008/086817 dated Jul. 6, 2010.

Preliminary Report on Patentability for PCT/US2008/071435 dated Feb. 9, 2010.

Preliminary Report on Patentability & Written Opinion for PCT/US2008/071539 dated Mar. 2, 2010.

EP Search Report for EP 06255566.5 dated Jun. 5, 2007.

* cited by examiner

BLEND HYDROGELS AND METHODS OF MAKING

This application claims the benefit of U.S. Provisional Application No. 60/656,453 filed Feb. 23, 2005, which is incorporated herein by reference in its entirety.

The present invention relates to blend hydrogels that may be suitable for use in biomedical or other applications.

BACKGROUND

Hydrogels are water-swellable or water-swollen materials whose structure is typically defined by a crosslinked or interpenetrating network of hydrophilic homopolymers or copolymers. The hydrophilic homopolymers or copolymers can be water-soluble in free form, but in a hydrogel they may be rendered insoluble due to the presence of covalent, ionic, or physical crosslinks. In the case of physical crosslinking, the linkages can take the form of entanglements, crystallites, or hydrogen-bonded structures. The crosslinks in a hydrogel provide structure and physical integrity to the polymeric network.

Hydrogels can be classified as amorphous, semicrystalline, hydrogen-bonded structures, supermolecular structures, or hydrocolloidal aggregates. Numerous parameters affect the physical properties of a hydrogel, including porosity, pore size, nature of gel polymer, molecular weight of gel polymer, and crosslinking density. The crosslinking density influences the hydrogel's macroscopic properties, such as volumetric equilibrium swelling ratio, compressive modulus, or mesh size. Pore size and shape, pore density, and other factors can impact the surface properties, optical properties, and mechanical properties of a hydrogel.

Hydrogels can attain a wide variety of mechanical properties. In general, however, hydrogels are observed to be pliable or rubbery, with a lubricious surface. Hydrogels are generally characterized by a low coefficient of friction owing to the water content and water-release properties at the surface. Frictional behaviors of hydrogels do not conform to Amonton's law, which states that the friction force is proportional to normal (i.e., orthogonal to the plane of motion) force. Unique load dependencies are observed for the friction coefficient of hydrogels: as load increases, friction coefficient decreases. As the hydrogel deforms under load, part of the water is squeezed out from the bulk gel and serves as a lubricant, leading to boundary lubrication or hydrodynamic lubrication.

Hydrogels have been fabricated from a variety of hydrophilic polymers and copolymers. Poly (vinyl alcohol), poly (ethylene glycol), poly(vinyl pyrrolidone), polyacrylamide, and poly(hydroxyethyl methacrylate), and copolymers of the foregoing, are examples of polymers from which hydrogels have been made.

Hydrogels can be neutral or ionic based on the type of charges of any pendent groups on the polymer chains. Hydrogels may exhibit swelling behavior that is dependent on and responsive to the external environment. Environmentally or physiologically responsive hydrogels, sometimes referred to as "intelligent" hydrogels, can exhibit drastic changes in swelling ratio due to changes in the external pH, temperature, ionic strength, nature of the swelling agent, and exposure to electromagnetic radiation. Hydrogels that exhibit pH-dependent swelling behavior generally contain either acidic or basic pendant groups. In aqueous media of appropriate pH and ionic strength, the pendent groups can ionize, resulting in fixed charges on the gel.

Over the past three to four decades, hydrogels have shown promise for biomedical and pharmaceutical applications, mainly due to their high water content and rubbery or pliable nature, which can mimic natural tissue. Biocompatible hydrogels can be engineered to be either degradable or resistant to degradation. An additional advantage of hydrogels, which has only recently been appreciated, is that they may provide desirable protection of drugs, peptides, and especially proteins from the potentially harsh environment in the vicinity of a release site. Thus, such hydrogels could be used as carriers for the delivery of proteins or peptides by a variety of means, including oral, rectal, or in situ placement. Transport of eluents either through or from a hydrogel is affected by pore size and shape, pore density, nature of polymer, degree of hydration, and other factors. Hydrogels can also act as transport barriers, due to a size exclusion phenomenon. Also relevant in drug delivery applications are pH and ionic strength sensitivity, as exhibited by hydrogels of some ionic or ionizable polymers.

Hydrogels have been used and proposed for a wide variety of biomedical and drug-delivery applications. For example, hydrogels have been utilized in controlled-release devices to achieve delivery of a drug or protein over time, and hydrogels have been widely employed in the fabrication of contact lenses. Hydrogels can be made to have properties similar to cartilage and are one of the most promising materials for meniscus and articular cartilage replacement. An overview of considerations for biological and medical applications of hydrogels can be found in Peppas, et al., *Ann. Rev. Biomed. Eng.* 2, 9 (2000), which is incorporated by reference in its entirety.

Poly(vinyl alcohol) ("PVA") is a polymer that has been studied extensively for potential biomedical applications. PVA hydrogels can be produced, for example, from aqueous solution via repeated freezing and thawing cycles that increase the order of the crystals, changing the dissolution properties, mesh size, and diffusion properties of the polymer. PVA gels that are prepared by freezing and thawing techniques have shown improved properties over hydrogels prepared by traditional chemical crosslinking techniques. In particular, increased mechanical strength has been obtained, due to the existence of localized crystalline regions that serve as physical crosslinks. The crystalline regions are thought to aid in distributing a given mechanical load or stress.

An overview of developments in PVA hydrogels can be found in Peppas, et al., *Adv. Polymer Sci.* 153, 37 (2000), which is incorporated by reference in its entirety.

One desirable feature of PVA hydrogels for biomedical applications is that the hydrogels can be superabsorbent. PVA hydrogels can have a moisture content of upwards of 70% in many cases. In contrast, polyurethane hydrogels commonly employed in implantable devices are generally characterized by low moisture content, on the order of a few percent.

Problems commonly associated with hydrogels that possess superabsorbent properties include low mechanical strength and low shear strength. Devices made from PVA hydrogels have been observed to fail due to wear, such as by tearing, abrasion, or shredding. For implants made from PVA hydrogels, achieving satisfactory fixation to bone or other tissue has also been an obstacle.

SUMMARY OF THE INVENTION

The present invention provides a water-swellable material comprising a blend of polymers including at least one hydrophilic polymer and at least one other polymer or oligomer having hydrophobic and hydrophilic character. The hydrophilic polymer may be poly(vinyl alcohol), for example. By way of illustration only, other hydrophilic polymers that may be suitable include poly(hydroxyethyl methacrylate), poly (vinyl pyrrolidone), poly(acrylamide), poly(acrylic acid), hydrolyzed poly(acrylonitrile), poly(ethyleneimine), ethoxylated poly(ethyleneimine), poly(allylamine), and poly(glycols).

In one embodiment, the present invention provides a water-swellable material comprising a blend of poly(vinyl alcohol) and a polymer or oligomer having hydrophobic recurring units and hydrophilic recurring units. The polymer or oligomer may be poly(ethylene-co-vinyl alcohol), for example. As non-limiting examples, other suitable polymers or oligomers include diol-terminated poly(hexamethylene phthalate) and poly(styrene-co-allyl alcohol).

In some embodiments, the water-swellable materials are thermoplastic before being hydrated, and can be melt processed by using an appropriately chosen diluent or plasticizer, which may include dimethylsulfoxide.

The invention also provides a hydrogel in hydrated form, comprising a blend of at least one hydrophilic polymer and at least one polymer or oligomer having hydrophobic character and hydrophilic character. The hydrogels can be made using the water-swellable materials described herein, for instance.

In one embodiment, the invention provides a hydrogel in hydrated form, comprising a blend of polymers including poly(vinyl alcohol) and a polymer or oligomer having hydrophobic and hydrophilic recurring units. In some embodiments, the blend hydrogel is characterized by a percent hydration in the range from about 10% -90%, and more suitably in the range from about 20%-85%. As used herein, a percent hydration represents the proportion of water to overall weight; a percent hydration of 75% means that the hydrogel is 75% water and 25% solids, for example.

A method for making a water-swellable material is also provided by the present invention. In one embodiment, the method comprises a) dissolving a blend of polymers in a suitable polar solvent including at least a minor fraction of water; b) cooling the solution to a temperature of 0° C. or below, to cause at least partial physical crosslinking of the polymers; and c) warming the crosslinked blend to above 20° C., to provide the water-swellable material. In some embodiments of the method, the polar solvent is dimethyl sulfoxide. Other suitable solvents may include dimethylformamide, dimethylacetamide, and tetrahydrofuran.

In another embodiment, the method comprises a) forming a blend of polymers in a melt at a temperature above 80° C. using a suitable polar solvent including at least a minor fraction of water; b) compression-molding the melt into a desired shape; c) cooling the component to a temperature of 0° C. or below, to cause at least partial physical crosslinking of the polymers; and d) warming the crosslinked blend to above 20° C., to provide the water-swellable material. In some embodiments of the method, the polar solvent is dimethyl sulfoxide. Other suitable solvents may include dimethylformamide, dimethylacetamide, and tetrahydrofuran.

The water-swellable materials and hydrogels of the present invention may be suitable for use in a wide variety of applications, including tissue replacement or augmentation, other biomedical applications, and non-biomedical applications.

DETAILED DESCRIPTION

Figure 1:
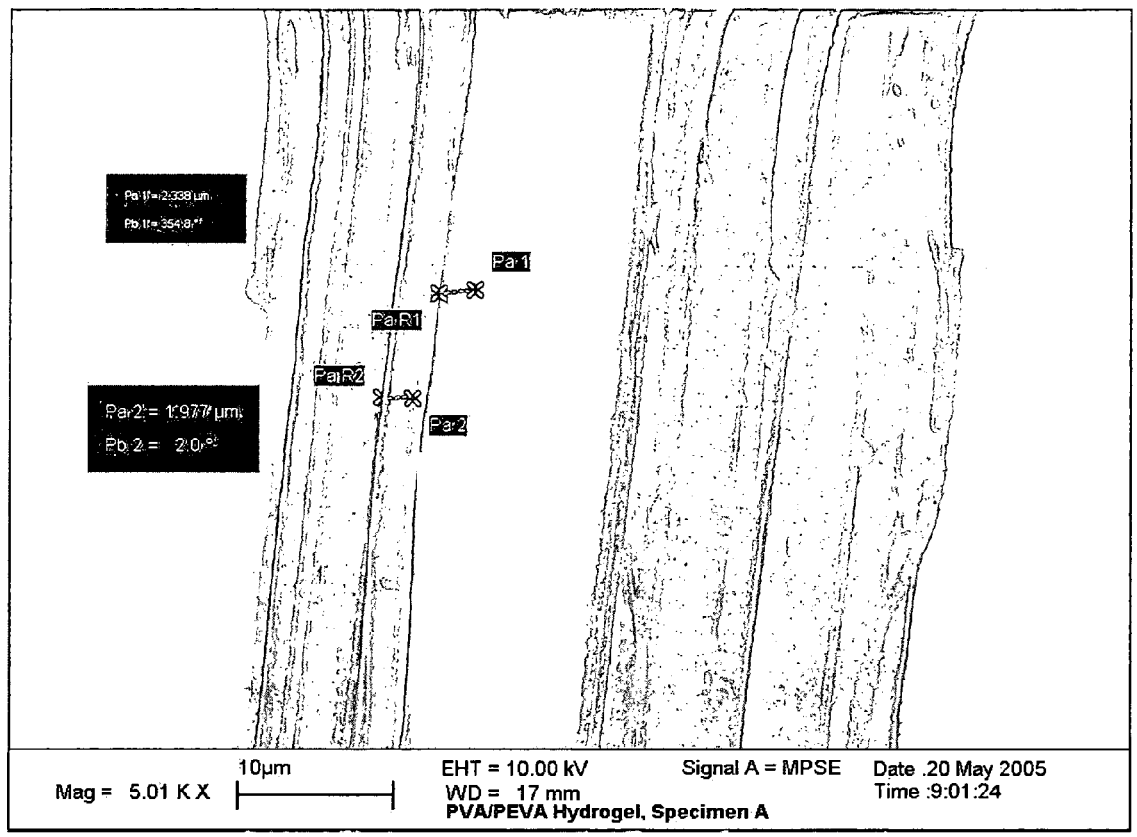
FIG. 1 is a digital image of hydrogel microfibers formed by extrusion.

For clarification of definitions for any terms relating to polymers, please refer to "Glossary of Basic Terms in Polymer Science" as published by the International Union of Pure and Applied Chemistry ("IUPAC"), *Pure Appl. Chem.* 68, 2287-2311 (1996). However, any definitions explicitly set forth herein should be regarded as controlling.

Unless the context indicates otherwise, the terms copolymer, monomer and similar terms also include mixtures and combinations of such materials. Furthermore, the term copolymer should be interpreted to include terpolymers, etc. Unless otherwise specified, all stated percentages and ratios are given by weight.

One approach for improving or customizing hydrogel properties is to use a blend of polymers in the hydrogel. For example, a blend of polymers can be employed as a means to change the water retention properties of a hydrogel, to change the environmental responsiveness of a hydrogel, or to reinforce the network structure of a hydrogel.

PVA-based blend hydrogels have been made in which PVA is blended with another homopolymer or copolymer during manufacture of the hydrogel. For example, a hydrogel formed from a blend of PVA and acrylic acid (AA) was reported by Hickey, et al., *Polymer* 38, 5931(1997). The PVA/AA blend hydrogels were reported to be sensitive to environmental pH. Hydrogel blends of PVA and poly(vinyl pyrrolidone) (PVP) have also been made.

Water-Swellable Material

The present invention provides a water-swellable material comprising a blend of polymers including a hydrophilic polymer and another or a second polymer or oligomer having hydrophobic and hydrophilic character. In this specification, the term polymer having hydrophobic and hydrophilic character incudes both polymers and oligomers. The hydrophilic polymer may be poly(vinyl alcohol) ("PVA"), for example. By way of illustration only, other hydrophilic polymers that may be suitable include poly(hydroxyethyl methacrylate), poly(vinyl pyrrolidone), poly(acrylamide), poly(acrylic acid), hydrolyzed poly(acrylonitrile), poly(ethyleneimine), ethoxylated poly(ethyleneimine), poly(allylamine), poly(glycols) as well as blends or mixtures of any of these hydrophilic polymers.

In certain embodiments, the present invention provides a water-swellable material comprising a crosslinked blend including poly(vinyl alcohol) and a second polymer having hydrophobic recurring units and hydrophilic recurring units. In some embodiments, the water-swellable material before being hydrated is a thermoplastic material.

As used herein to describe the present invention, the term "water-swellable" indicates that the material is able to take on and retain water within a network of polymers, and does not imply that a change in volume of the material necessarily occurs upon hydration.

In certain embodiments, the water-swellable material includes poly(vinyl alcohol) as one component, and a second polymer having hydrophobic recurring units and hydrophilic recurring units as another component. The second polymer may be a copolymer such as poly(ethylene-co-vinyl alcohol), for example.

The water-swellable material may also include additional polymers, or conventional additives such as plasticizers, components for inhibiting or reducing crack formation or propagation, components for inhibiting or reducing creep, or particulates or other additives for imparting radiopacity to the material. By way of example only, an additive for imparting radiopacity can include metal oxides, metal phosphates, and metal sulfates such as those of barium sulfate, barium titanate, zirconium oxide, ytterbium fluoride, barium phosphate, and ytterbium oxide.

The blend may comprise from about 5%-95% by weight of the hydrophilic polymer, and about 5%-95% by weight of the second polymer. More suitably, the blend comprises from about 30%-95% by weight of the hydrophilic polymer, and about 5%-70% by weight of the second polymer. In some embodiments, the blend comprises from about 50%-95% by weight of the hydrophilic polymer, and about 5%-50% by weight of the second polymer.

In another embodiment comprising poly(vinyl alcohol), the blend may comprise from about 5%-95% by weight of poly(vinyl alcohol), and about 5%-95% by weight of the second polymer. More suitably, the blend comprises from about 30%-95% by weight of poly(vinyl alcohol), and about 5%-70% by weight of the second polymer. In some embodiments, the blend comprises from about 50%-95% by weight of poly(vinyl alcohol), and about 5%-50% by weight of the second polymer. In one embodiment, the blend comprises about 50% by weight of poly(vinyl alcohol) and about 50% by weight of the second polymer. In any of the foregoing embodiments, the water-swellable material may be a blend of poly(vinyl alcohol) and poly(ethylene-co-vinyl alcohol) as the second polymer.

In other embodiments, the blend comprises or consists essentially of about 5%-95% by weight of poly(vinyl alcohol) and about 5%-95% by weight poly(styrene-co-allyl alcohol) as the second polymer. In still other embodiments, the blend comprises or consists essentially of about 5%-95% by weight of poly(vinyl alcohol) and about 5%-95% by weight diol-terminated poly(hexamethylene phthalate) as the second polymer.

Methods of processing to obtain a water-swellable material of desired shape or size include solution casting, injection molding, or compression molding. In general, these methods may be used prior to or after crosslinking by a freeze-thaw method or other means or steps for crosslinking.

In some embodiments, the water-swellable material in the form of a hydrogel is a thermoplastic and can be melted and re-solidified without losing its water-swellable character. A lyogel is a term generally used to describe the physical state of a hydrogel material or article before the solvent used to prepare the material or article is replaced with water. In one embodiment, the material is a thermoplastic characterized by a melting temperature in the range from about 70° C.-200° C. The thermoplastic quality of the water-swellable material allows for easy processability and end use. Upon melting, the material becomes flowable and can therefore be extruded, injected, shaped, or molded.

In certain embodiments at least one component of the blend is PVA. PVA for commercial use is generally produced by free-radical polymerization of vinyl acetate to form poly(vinyl acetate), followed by hydrolysis to yield PVA. The hydrolysis reaction does not go to completion, which leaves pendent acetate groups at some points along the polymer chain. In practice PVA can therefore be thought of as a copolymer of vinyl acetate and vinyl alcohol. The extent of the hydrolysis reaction determines the degree of hydrolysis of the PVA. Commercially available PVA can have a degree of hydrolysis over 98% in some cases.

The degree of hydrolysis (which indicates the number of remaining pendent acetate groups) affects the solubility, chemical properties, and crystallizability of PVA. PVA having a very high degree of hydrolysis (greater than 95%) is actually less soluble in water than PVA having a lower degree of hydrolysis, due to the high degree of intra-chain hydrogen bonding by the hydroxyl groups. For PVA having a lower degree of hydrolysis, the residual acetate groups weaken the intramolecular and intermolecular hydrogen bonds and enable solvation by water.

Similarly, the presence of residual acetate groups also affects the crystallizability of PVA. PVA having a high degree of hydrolysis is more difficult to crystallize than PVA having a lower degree of hydrolysis. Crystalline PVA is reported to have a glass transition temperature of about 85° C., and melt in the range of 220° to 240° C. The presence of water or other solvents in crystalline PVA reportedly depresses the glass transition temperature significantly from that of pure PVA. See Peppas, et al., *Adv. Polymer Sci.* 153, 37 (2000).

Commercially available PVA is generally characterized by a fairly wide molecular weight distribution. A polydispersity index of 2 to 2.5 is common for commercial PVA, and a polydispersity index of up to 5 is not uncommon. The molecular weight distribution of PVA affects properties such as crystallizability, adhesion, mechanical strength, and diffusivity.

For use in the present invention, PVA is desired to have an average molecular weight above 50 kDa and a degree of hydrolysis above 70%. More commonly, the PVA has an average molecular weight above 80 kDa and a degree of hydrolysis above 90%. In one embodiment, the PVA is characterized by an average molecular weight in the range from about 86 kDa to 186 kDa.

A second component of the blend is a polymer having both hydrophobic and hydrophilic character. Generally the second polymer will include hydrophobic and hydrophilic recurring units. The polymer can be a copolymer, for example. It may be possible to vary or adjust the "stiffness" of the water-swellable material, or the hydrogel that results from hydration of the material, by varying the overall hydrophobicity or hydrophilicity of the polymer. This may be due to a greater or lesser number of crosslinking sites.

In some embodiments, the hydrophobic recurring units comprise an aliphatic hydrocarbon segment. Aliphatic hydrocarbon recurring units may take the form $—[CH_2CH_2—]$ or $—[CH_2CH(CH_3)—]$, for example. In other embodiments, hydrophobic recurring units can comprise aliphatic, cyclic, or aromatic hydrocarbon pendent groups (e.g., pendant phenyl groups), or heterocyclic or heteroaromatic pendent groups. By way of example only, the hydrophobic region can also comprise or consist of fluorocarbon segments, segments comprising cyano pendant groups, or segments comprising imide groups.

In one embodiment, a majority of the hydrophobic recurring units are of the form $—[CH_2CH_2—]$. As used herein, the term "majority" means at least 50%. In another embodiment, the hydrophobic recurring units are predominantly of the form $—[CH_2CH_2—]$. As used herein, the term "predominantly" means a high proportion, generally at least 90%.

The hydrophilic recurring units of the polymer include recurring units having hydrophilic groups, such as hydroxyl carboxylic acid or sulfonic acid pendent groups, hydrophilic heterocyclic groups such as pyrrolidone pendent groups, or alkylene oxide groups (e.g., ($C_1$-$C_6$) alkylene oxide groups, more typically ($C_1$-$C_3$) alkylene oxide groups, such as $—[CH_2O—]$, $—[CH_2CH_2O—]$, $—[CH(CH_3)O—]$, $—[CH_2CH_2CH_2O—]$, $—[CH(CH_3)CH_2O—]$, $—[CH_2CH(CH_3)O—]$) in the polymer backbone or as pendant groups.

In one embodiment, a majority of the hydrophilic recurring units comprise pendant hydroxyl groups. In another embodiment, the hydrophilic recurring units predominantly comprise pendant hydroxyl groups. In one embodiment, a majority of the hydrophilic recurring units are of the form —[CH$_2$CH(OH)—]. In another embodiment, the hydrophilic recurring units predominantly are of the form —[CH$_2$CH (OH)—].

A copolymer derived from a hydrophobic monomer and a hydrophilic monomer may be suitable as the polymer, for example. One suitable copolymer comprises recurring units of the form —[CH$_2$CH$_2$—] and recurring units of the form —[CH$_2$CH(OH)—], for example. In one embodiment, the copolymer comprises recurring units of the form —[CH$_2$CH$_2$—] and recurring units of the form —[CH$_2$CH (OH)—] in a ratio in the range from about 1:1 to about 1:3.

One specific example of a suitable copolymer is poly(ethylene-co-vinyl alcohol), also known as "EVAL" "PEVAL" or "EVOH." Poly(ethylene-co-vinyl alcohol) can be formed into a hard, crystalline solid and is used commercially in food packaging and other applications. All of the commercially available grades of poly(ethylene-co-vinyl alcohol) are suitable for use in preparing hydrogels. Commercially available grades are available having an ethylene content, expressed as a mole-percent, of 26%-29%, 32%, 35%, 44%, and 48%. Other copolymers having hydrophilic recurring units and hydrophobic recurring units that may be suitable include poly(ethylene-co-acrylic acid) and poly(ethylene-co-methacrylic acid). A specific example of a suitable copolymer include poly(styrene-co-allyl alcohol) (such as poly(styrene-co-allyl alcohol) with an average molecular weight of ~1600).

A block copolymer having hydrophobic blocks and hydrophilic blocks may also suitable as the polymer. A suitable block copolymer could be derived from Oligomers or prepolymers having the hydrophobic and hydrophilic segments.

Hydrophobic polymers or oligomers with hydrophilic end groups may also be suitable as the polymer. A specific example of a suitable oligomer having hydrophilic end groups is diol-terminated poly(hexamethylene phthalate) (such as a diol-terminated poly(hexamethylene phthalate) with an average molecular weight of ~1000).

By way of illustration only, other polymers with hydrophilic and hydrophobic character that may suitable include dicarboxy-terminated poly(acrylonitrile-co-butadiene), poly (3,3',4,4'-biphenyltetracarboxylic dianhydride-co-1,4-phenylenediamine) amic acid, poly(3,3',4,4'-benzophenonetetracarboxylic dianhydride-co-4,4'-oxydianiline/1,3-phenylenediamine) amic acid, poly(bisphenol A-co-4-nitrophthalic anhydride-co-1,3-phenylenediamine), polybutadiene epoxy/hydroxyl functionalized, hydroxyl-terminated polybutadiene, poly(ethylene-co-1,2-butylene)diol, hydroxyl-terminated poly(hexafluoropropylene oxide), and glycidyl end-capped poly(bisphenol A-co-epichlorohydrin).

The water-swellable material may optional be a crosslinked blend of the polymers described above. Crosslinking can be achieved by a variety of means or steps, including physical crosslinking, chemical crosslinking, electron-beam irradiation, or gamma irradiation.

Physical crosslinking may be achieved by the freeze-thaw solution-phase methods described below, for example, or by conventional freeze-thaw techniques known in the art of PVA hydrogels. Such methods are described in the scientific literature and patents cited herein, including Peppas, et al., *Adv. Polymer Sci.* 153, 37 (2000) and the references cited therein. Freeze-thaw methods are thought to cause hydrogen bonding between the hydrophilic groups of the polymers. One advantage of a freeze-thaw technique is that it permits the water-swellable material to be manufactured without the use of potentially toxic solvents or chemical crosslinking agents, initiators, and the like. Briefly, it is known that repeated cycles of freezing at −20° C. and thawing at 25° C. result in the formation of crystalline regions that remain intact upon being placed in contact with water or biological fluids at 37° C. Similar or identical parameters for freeze-thaw cycles are suitable in the practice of the present invention.

In one embodiment of the method, the solution is cooled to a temperature of 0° C. or below, to cause at least partial physical crosslinking of the polymers and produce a crosslinked blend. In another embodiment of the method, the solution is cooled to a temperature of 0° C. or below for a time period of at least 2 hours, more suitably at least 3 hours, and in some embodiments 12 hours or longer. The crosslinked blend is subsequently warmed to above 20° C., generally to room temperature (~27° C.) to provide the water-swellable material.

Chemical crosslinking is also known in the art. Examples of suitable chemical crosslinking agents include monoaldehydes such as formaldehyde, acetaldehyde, or glutaraldehyde in the presence of sulfuric or acetic acid or methanol. Other suitable crosslinking agents include diisocyanate compounds, which can result in urethane linkages, or epoxy compounds. Crosslinking achieved using enzymes or salts of divalent metals (e.g., $Zn^{2+}$) is also known in the field, and is suitable in the practice of the present invention.

Crosslinking by irradiation using laser, electron-beam or gamma irradiation, may also be suitably employed in the practice of the present invention. A combination of means or steps for crosslinking may be utilized in the invention. For example, a freeze-thaw cycle could be used to provide physical crosslinking, followed by electron-beam or gamma irradiation to provide more complete crosslinking. As other examples, chemical crosslinking could be followed by laser, electron-beam or gamma irradiation, or a freeze-thaw step could be done after crosslinking by any of chemical, laser, electron-beam or gamma irradiation. A combination approach may be suitable for providing additional strength or resilience to the resulting material. By way of example only, a combination of means or steps for crosslinking may be sufficient to address problems of creep that might arise when only one means or step is used.

Blend Hydrogel

The invention also provides a blend hydrogel. A blend hydrogel may be formed by hydrating the water-swellable materials described above. Hydration can be caused by contacting the water-swellable material with water, an aqueous solution, or a biological fluid, for example.

The water-swellable material will generally reach an equilibrium hydration level if left in contact with water or an aqueous fluid. The hydrogels of the present invention can achieve a high water content (e.g., about 70% or greater), approaching or comparable to levels observed for known "superabsorbent" hydrogels. In one embodiment, the blend hydrogel is characterized by a percent hydration in the range from about 10%-90%, more suitably in the range from about 20%-85%, and often in the range from about 50%-70%.

Upon contact with water, the water-swellable material become immiscible and exhibits a phase separation between "crystalline" and "non-crystalline" regions in some embodiments. Onset of phase separation is often indicated in a polymeric film or solid by a transition from a transparent or colorless state to a translucent or opaque state often exhibiting a white color.

For many of the water-swellable materials of the present invention, the phase separation has been observed to be specific to the presence of water. Contact with water swells the water-swellable material, which may increase the free volume and allow main-chain motion. The swelling allows phase separation and induces the opaque, white color. It has been observed that dehydration returns the water-swellable material to its original translucent state. Repeated swelling and dehydration has not been observed to cause any noticeable changes in material behavior.

The hydrogels of the present invention possess a unique set of mechanical properties. In certain embodiments, the materials exhibit toughness comparable or superior to other hydrogels including PVA-based hydrogels, while maintaining flexibility and a low elastic modulus. Examples of these improved properties are increased tensile strength, increased shear resistance, and improved elasticity. Furthermore, the properties of the hydrogels can be tailored to meet the requirements for a specific usage.

Method of Making a Water-Swellable Material

In another embodiment, the present invention provides a method of making a water-swellable material. The method comprises the steps of dissolving a blend of polymers in a suitable polar solvent including at least a minor fraction of water (~0-30%), cooling the solution to a temperature of 0° C. or below, to cause at least partial physical crosslinking of the polymers, and warming the crosslinked blend to 20° C. or above, to provide the water-swellable material. The method may optionally include a step to extract the polar solvent or other impurities from the crosslinked blend, by contacting the crosslinked blend with a second solvent. Additional freeze-thaw cycles may also be employed in the method. The use of irradiation may also be employed to provide additional crosslinking.

Another method provided by the present invention comprises melt-processing the blend of polymers in a suitable polar plasticizer or diluent, which may contain a fraction of water (~0-30%), in a heated mixing device such as a twin-screw compounder. The material may be further processed in an injection molding machine or compression molder at an elevated temperature, generally above ~80° C. dependent on plasticizer/diluent and the polymer blend. The molded components are then further processed to provide crosslinking, such as using irradiation or freeze-thaw methods as described herein. In the case of gamma irradiation, molded parts are irradiated between 20-100 kGy with a preferred dose of 30-60 kGy.

Suitable polymer blends are described above with respect to the water-swellable material of the invention. The polar solvent or plasticizer/diluent should be chosen so that both the hydrophilic polymer component (such as poly(vinyl alcohol)) and the second polymer are at least partially soluble in the polar solvent. The descriptions of solvents, and plasticizers/diluents given below should be regarded as interchangeable, as it is thought that similar components can be used for either purpose.

Suitable polar solvents are known in the field of PVA hydrogels, for example. Solvents such as glycerine, ethylene glycol, propylene glycol, and ethanol have been used to make PVA hydrogels, and may be suitable for the practice of the present invention. Other solvents may include tetrahydrofuran, toluene, dimethylformamide, dimethylacetamide, acetone, acetonitrile, cyclohexane, cyclopentane, 1,4-dioxane, ethyl acetate, glyme, methyl tert-butyl ether, methyl ethyl ketone, pyridine, water, and chlorobenzene.

A solvent commonly used in the formation of PVA hydrogels is dimethyl sulfoxide, ("DMSO"). DMSO has been found to be particularly suitable for the practice of the invention. In one embodiment, the solvent comprises at least about 97% DMSO, by weight. In an alternative embodiment, the solvent comprises 70 to 80 parts DMSO: 20 to 30 parts water. In some embodiments, the solvent consists essentially of DMSO and water.

In most cases, small amounts of a secondary solvent, such as water, aids in the formation of the hydrogel component. It is believed that at least a minor fraction of water needs to be present in the solvent in order to inhibit undesired phase separation and to achieve suitable crosslinking during the crosslinking step. The presence of too little water can lead to crystallinity with large phase separation prior to crosslinking or exposure to water, which may be undesirable for some applications. However, the presence of too much water may lead to an immiscible blend during the processing steps.

In an alternative embodiment, the solvent can include saline or some other physiological solution. The use of saline in manufacturing PVA hydrogels is described, for example, by Hassan, et al., *J. Appl. Poly. Sci.* 76, 2075 (2000). PVA hydrogels made in the presence of saline were reported to exhibit enhanced swelling kinetics and greater overall water content. As another embodiment, the solvent can include growth factors, analgesics, antibiotics, stem cells, or osteochondral cells.

To prepare a solution for use in casting, the appropriate polymers (and optionally any additives) are dissolved in the solvent. Heating the solvent may assist in dissolution of the polymers. The polymer-to-solvent ratio can vary widely. PVA hydrogels, by way of illustration, have reportedly been prepared using a polymer concentration of 2%-50% by weight. In one embodiment of the method, the solution comprises about 0.5 parts of the polymer blend per one part solvent, by weight.

To prepare a material for compression or injection molding, the appropriate polymers (and optionally any additives) can be compounded in a heated mixing device such as a twin-screw compounder with the appropriate diluent/plasticizer. Heating the mixing device may assist in processing. Suitable temperatures depend on diluent/plasticizer and the chosen polymer system. In one embodiment of the method, the processing temperature ranges from 80° C. to 130° C., and more suitably in the range from 90 to 115° C. The polymer-to-diluent ratio can vary widely. In one embodiment of the method, the blend material comprises about 0.5 parts of polymer blend per one part solvent, by weight.

In an optional step, the blend is contacted with a second solvent in order to extract the polar solvent from the interstices or pores of the crosslinked blend. Extraction of the polar solvent may facilitate the subsequent hydration of the resulting water-swellable material, and can also serve to remove undesirable components (such as crosslinking agents or short, non-crosslinked fragments of PVA) from the water-swellable material.

The second solvent will generally be an organic solvent that is at least slightly to moderately polar. In practice, it may also be desirable to use a volatile solvent that can be readily dried or evaporated. Suitable solvents include lower alkyl alcohols (e.g., methanol, ethanol, n-propanol, isopropanol, etc.), ethers, or ketones, for instance. A mixture of solvents may also be employed.

By way of example, it has been determined that ethanol is an adequate solvent for extracting DMSO from the crosslinked blend, when DMSO is employed as the polar solvent. Immersing the crosslinked blend in ethanol for a period of time is sufficient to enable the extraction of the polar solvent. To assure complete extraction, it may be necessary to remove spent solvent and replenish with the second solvent (or another suitable solvent) one or more times.

In one embodiment of the invention, the solvent extraction step is done simultaneously with a thaw cycle; i.e., the blend is placed in contact with a second solvent as it is warmed from a freezing temperature. In another embodiment, the blend may remain in contact with the second solvent during subsequent freeze-thaw cycles. In a third embodiment, the solvent extraction step is done at room temperature after the thaw cycle.

In Vivo Delivery of Thermoplastic Water-Swellable Material

As discussed above, the water-swellable material of the present invention is a thermoplastic in some embodiments, and can be melted and re-solidified while retaining its water-swellable character. The thermoplastic quality of the water-swellable material allows for easy processability. Upon melting, the material becomes flowable and can be extruded, shaped, or molded to a desired configuration.

It has been observed that in some embodiments the water-swellable material is also characterized by either low heat capacity or poor thermal conductivity, and can be manually handled in a heated, flowable state without special precautions. Melt-processability allows the water-swellable material to be manipulated so that in situ delivery and shaping can be accomplished. Therefore, the thermoplastic water-swellable material may be directly injected into the body of a patient, to allow for in situ formation of a hydrogel material. Such a technique may have practical application in several minimally invasive surgical procedures, as further described below.

In another embodiment, the invention provides for the use of a thermoplastic water-swellable material in conjunction with a means or step for heating and a means or step for in vivo delivery. The means for heating can be any conventional heat source that would permit the water-swellable material to be heated to a temperature at which it can flow. An example of a suitable means for heating is a hot gun. The means for delivery can be any suitable device, such as a delivery tube or a needle. In some embodiments, the means for heating and means for delivery can be combined into one physical device. By way of example, a heated delivery tube could serve to provide both functions.

In Vivo Use of Blend Hydrogel

The blend hydrogels may be used in a number of biomedical applications including cartilage replacement or augmentation and spinal disc replacement, augmentation, or rehabilitation.

The hydrogels of the present invention can be highly hydrated, and exhibit higher strength and tear resistance compared to typical PVA hydrogels in some embodiments. The hydrogels can be engineered to exhibit tissue-like structure and properties. Where the water-swellable material is a thermoplastic, the advantage of in situ formability can be put to use as described above. For such an application, the water-swellable material can be hydrated in vivo after delivery and formation, to provide a hydrogel. For applications where the water-swellable material can be formed to shape externally, the water-swellable material can be hydrated either in vivo or ex vivo/in vitro.

The water-swellable materials and hydrogels of the present invention can be made without the use of undesirable components that could cause an adverse reaction in the body, such as solvents, uncrosslinked polymer strands, and crosslinking agents, or can be processed to remove the undesirable components. Or, the water-swellable materials and hydrogels can include inhibitors to counteract adverse reactions.

The materials of the present invention can be used in a variety of applications, including minimally invasive surgical procedures. By way of example, the hydrogels can be used to provide artificial articular cartilage as described, e.g., by Noguchi, et al., *J. Appl. Biomat.* 2, 101 (1991). The hydrogels can also be employed as artificial meniscus or articular bearing components. The hydrogels can also be employed in temporomandibular joint, in proximal interphalangeal joint, in metacarpophalangeal joint, in metatarsalphalanx joint, or in hip capsule joint repair.

The water-swellable materials or hydrogels of the present invention can also be used to replace or rehabilitate the nucleus pulposus of an intervertebral disc. Degenerative disc disease in the lumbar spine is marked by a dehydration of the intervertebral disc and loss of biomechanical function of the spinal unit. A recent approach has been to replace only the central portion of the disc, called the nucleus pulposus. The approach entails a less invasive posterior surgery, and can be done rather rapidly. Bao and Higham developed a PVA hydrogel suitable for nucleus pulposus replacement, as described in U.S. Pat. No. 5,047,055. The hydrogel material, containing about 70% water, acts similarly to the native nucleus, in that it absorbs and releases water depending on the applied load.

The hydrogels of the present invention can be similarly employed in the manner described therein, or in other applications known in the field. The water-swellable materials of the invention can also be employed in a replacement method. Where the water-swellable material is a thermoplastic, the advantage of in situ formability can be put to use as described above. For such an application, the water-swellable material can be hydrated in vivo after delivery and formation, to provide a hydrogel.

The hydrogels of the invention can also be employed in a spinal disc prosthesis used to replace a part or all of a natural human spinal disc. By way of example, a spinal disc prosthesis may comprise a flexible nucleus, a flexible braided fiber annulus, and end-plates. The hydrogel may be employed in the flexible nucleus, for example. A spinal disc prosthesis is described in U.S. Pat. No. 6,733,533 to Lozier.

The ability of hydrogels to release therapeutic drugs or other active agents has been reported. The hydrogels of the present invention can be suitably employed in vivo to provide elution of a protein, drug, or other pharmacological agent impregnated in the hydrogel or provided on the surface of the hydrogel.

EXAMPLES

Synthesis of Water-Swellable Material

Blend Synthesis Example 1

To a 2000-mL beaker equipped with a mechanical stirrer was added 100 g poly(vinyl alcohol), 100 g poly(ethylene-co-vinyl alcohol), and 1100 mL of DMSO. The poly(vinyl alcohol) is 99+% hydrolyzed with an average molecular weight of 124 kDa to 186 kDa and was used as received from Sigma-Aldrich. The poly(ethylene-co-vinyl alcohol) was used as received from Sigma-Aldrich and contains 44 mole-percent ethylene. The DMSO was used as received from Sigma-Aldrich and contains ≦0.4% water. The solution was heated to 90° C. for three hours.

After three hours, the solution was poured into 9"×13" PYREX dishes heated to 80° C. The solution was allowed to cool slowly to room temperature, and the dish was then placed into a freezer at −30° C. for three hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 2

To a 2000-mL beaker equipped with a mechanical stirrer was added 100 g diol-terminated poly(hexamethylene phthalate), 100 g poly(vinyl alcohol), and 1100 mL of DMSO. The poly(vinyl alcohol) is 99+% hydrolyzed, with an average molecular weight of 124 kDa to 186 kDa and was used as received from Sigma-Aldrich. The diol-terminated poly(hexamethylene phthalate), with an average molecular weight of 1000 Da, was used as received from Sigma-Aldrich. The DMSO was used as received from Sigma-Aldrich and contains ≦0.4% water. The solution was heated to 90° C. for 1½ hours.

After 1½ hours, the solution was poured into 9"×13" PYREX dishes, covered, and placed in a 60° C. oven for 12 hours. The dish was then placed into a freezer at −30° C. for three hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 3

To a 2000-mL beaker equipped with a mechanical stirrer was added 100 g poly(styrene-co-allyl alcohol), 100 g poly(vinyl alcohol), and 1100 mL of DMSO. The poly(vinyl alcohol) is 99+% hydrolyzed with an average molecular weight of 124 kDa to 186 kDa and was used as received from Sigma-Aldrich. The poly(styrene-co-allyl alcohol), with an average molecular weight of 1200 Da, was used as received from Sigma-Aldrich. The DMSO was used as received from Sigma-Aldrich and contains ≦0.4% water. The solution was heated to 90° C. for three hours.

After three hours, the solution was poured into 9"×13" PYREX dishes and allowed to cool to room temperature. The dish was then placed into a freezer at −30° C. for twenty-four hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 4

To a 2000-mL beaker equipped with a mechanical stirrer was added 100 g poly(ethylene-co-vinyl alcohol), 100 g poly(vinyl alcohol), and 1100 mL of DMSO. The poly(vinyl alcohol) is 99+% hydrolyzed with an average molecular weight of 124 kDa to 186 kDa and was used as received from Sigma-Aldrich. The poly(ethylene-co-vinyl alcohol) with an ethylene content of 27 mole-percent was used as received from Sigma-Aldrich. The DMSO was used as received from Sigma-Aldrich and contains ≦0.4% water. The solution was heated to 90° C. for three hours.

After three hours, the solution was poured into 9"×13" PYREX dishes and allowed to cool to room temperature. The dish was then placed into a freezer at −30° C. for twelve hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

Blend Synthesis Example 5

To a 2000-mL beaker equipped with a mechanical stirrer was added 100 g poly(ethylene-co-vinyl alcohol), 200 g poly(vinyl alcohol), 200 mL deionized water, and 800 mL of DMSO. The poly(vinyl alcohol) is 99+% hydrolyzed with an average molecular weight of 86 kDa and was used as received from Acros. The poly(ethylene-co-vinyl alcohol) had an ethylene content of 27 mole-percent and was used as received from Sigma-Aldrich.

The DMSO was used as received from Sigma-Aldrich and contains ≦0.4% water. The solution was heated to 90° C. for three hours.

After three hours, the solution was poured into 9"×13" PYREX dishes and a hip cup mold. The material was allowed to cool to room temperature. The dish was then placed into a freezer at −30° C. for twelve hours. The dish was removed from the freezer. The material was allowed to warm to room temperature. The resulting material was translucent, flexible, and pliable. To extract the DMSO, 700 mL methanol was added to the resulting material. The resulting material remained translucent, flexible, and pliable.

Blend Synthesis Example 6

To a 1000-mL beaker equipped with a mechanical stirrer was added 10 g poly(ethylene-co-vinyl alcohol) [44 mole-percent ethylene], 10 g poly(ethylene-co-vinyl alcohol) [27 mole-percent ethylene], 20 g poly(vinyl alcohol), 3.8 g NANODENT, and 220 mL of DMSO. The poly(vinyl alcohol) is 99+% hydrolyzed with an average molecular weight of 86,000 and was used as received from Acros. The poly(ethylene-co-vinyl alcohol) had an ethylene content of 27 mole-percent and 44 mole-percent, as indicated, and was used as received from Sigma-Aldrich. The DMSO was used as received from Sigma-Aldrich and contains ≦0.4% water. The NANODENT is a radiopacifying agent, and was used as received from NanoSolutions. The solution was heated to 90° C. for three hours.

After three hours, the solution was poured into 9"×13" PYREX dishes and a hip cup mold. The material was allowed to cool to room temperature. The dish was then placed into a freezer at −30° C. for twelve hours. The dish was removed from the freezer.

The material was allowed to warm to room temperature. The resulting material was translucent, flexible, and pliable. To extract the DMSO, 700 mL propanol was added to the resulting material. The resulting material remained translucent, flexible, and pliable.

Blend Synthesis Example 7

To prepare material for a compression molder/injection molder, a HAAKE Polylab system equipped with a RheoMix was heated to 115° C. To the system was added 45 mL DMSO, 17.5 g of poly(ethylene-co-vinyl alcohol), and 17.5 g of poly(vinyl alcohol). The poly(vinyl alcohol) is 99+% hydrolyzed with an average molecular weight of 146 kDa to 186 kDa and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water.

The blend was allowed to mix for 10 minutes. The blend was removed from the mixer, allowed to cool to room temperature, and chopped. The resultant material was translucent and pliable.

Blend Synthesis Example 8

A blend was prepared as in Blend Synthesis Example 7, except that the poly(ethylene-co-vinyl alcohol) had an ethylene content of 27 mole-percent.

The blend was allowed to mix for 10 minutes. The blend was removed from the mixer, allowed to cool to room temperature, and chopped. The resultant material was translucent and pliable.

Blend Synthesis Example 9

To a 2000-mL beaker equipped with a mechanical stirrer was added 100 g poly(ethylene-co-vinyl alcohol) and 700 mL of DMSO. The poly(vinyl alcohol) is 99+% hydrolyzed with an average molecular weight of 146 kDa to 186 kDa and was used as received from Sigma Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water. The solution was heated to 90° C. for 12 hours.

Then, 100 g of poly(vinyl alcohol), 200 mL DMSO, and 5 g of p-toluene sulfonic acid monhydrate was added the solution as a pH modifier. The p-toluene sulfonic acid monohydrate was 98.5% pure ACS reagent-grade and was used as received from Sigma-Aldrich. The solution was heated to 90° C. for three hours.

After three hours, the solution was poured into 5" polyethylene bowls and cooled to −55° C. using a methanol/liquid nitrogen slush bath for approximately 30 minutes. A white frozen material resulted.

Blend Synthesis Example 10

To a 2000-mL beaker equipped with a mechanical stirrer was added 150 g poly(ethylene-co-vinyl alcohol), 50 g poly (vinyl alcohol), 200 mL deionized water, and 800 mL of DMSO. The poly(vinyl alcohol) is 99+% hydrolyzed with an average molecular weight of 146,000 to 186,000 and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water. The solution was heated to 90° C. for three hours.

After three hours, the solution was poured into 9"×13" PYREX dishes and a hip cup mold. The material was allowed to cool to room temperature. The dish was then placed into a freezer at −30° C. for twelve hours. The dish was removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

Blend Synthesis Example 11

To a 1000-mL beaker equipped with a mechanical stirrer was added 20 g poly(vinyl alcohol), 175 mL dimethyl sulfoxide, and 10 mL water. The solution was heated to 80° C. for 2 hours. To the solution was added 20 g poly(trimellitic anhydride chloride-co-4,4'-methylene-dianiline) and stirred for 1 hour at 120° C. The poly(vinyl alcohol) was 99+% hydrolyzed with an average molecular weight of 146,000 to 186,000 and was used as received from Sigma-Aldrich. The poly (trimellitic anhydride chloride-co-4,4'-methylene-dianiline) was used as received from Sigma-Aldrich and contained <1.0% of 4,4'-methylenedianiline. The DMSO was used as received from Sigma-Aldrich and contains ≦0.4% water. The solution was heated to 90° C. for three hours.

The solution was poured between two 8"×8"×0.05" glass plates. The material was allowed to cool to room temperature. The dish was then placed into a freezer at −30° C. for twelve hours. The dish was removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

Blend Synthesis Example 12

To a Jaygo 1 gallon sigma mixer/extruder fitted with a 3 mm fiber die was added 625.89 g poly(ethylene-co-vinyl alcohol), 100 mL of water, 1350 g dimethyl sulfoxide, and 626.79 g poly(vinyl alcohol). The materials were mixed at 240° F. for 70 minutes. The poly(vinyl alcohol) is 99+% hydrolyzed with an average molecular weight of 146,000 to 186,000 and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water.

After 70 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Blend Synthesis Example 13

To a Jaygo 1 gallon sigma mixer/extruder fitted with a 3 mm fiber die was added 626.66 g poly(ethylene-co-vinyl alcohol), 128.2 mL of water, 1438.2 g dimethyl sulfoxide, and 625.73 g poly(vinyl alcohol). The materials were mixed at 228° F. for 90 minutes. The poly(vinyl alcohol) is 99+% hydrolyzed with an average molecular weight of 146,000 to 186,000 and was used as received from Sigma-Aldrich. The poly(ethylene-co-vinyl alcohol) had an ethylene content of 32 mole-percent and was used as received from Sigma-Aldrich. The DMSO was used as received from Sigma-Aldrich and contains ≦0.4% water.

After 90 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Blend Synthesis Example 14

To Jaygo 1 gallon sigma mixer/extruder fitted with a 3 mm fiber die was added 402.44 g poly(ethylene-co-vinyl alcohol), 97.84 mL of water, 1400 g diethyl sulfoxide, and 850.02 g poly(vinyl alcohol). The materials were mixed at 228° F. for 50 minutes. The poly(vinyl alcohol) is 99+% hydrolyzed with an average molecular weight of 146,000 to 186,000 and was used as received from Sigma-Aldrich. The poly(ethylene-co-vinyl alcohol) had an ethylene content of 32 mole-percent and was used as received from Sigma-Aldrich. The DMSO was used as received from Sigma-Aldrich and contains ≦0.4% water.

After 50 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Hydrogels and Mechanical Properties Thereof

The water-swellable materials obtained from Blend Synthesis Examples 1-6, 9, 10, and 11 were immersed in water. For the water-swellable material from Blend Synthesis Example 9, the frozen material was immersed in water while still cold, while the others were immersed at room temperature. In each case, the material took on water and became a white, opaque, flexible hydrogel.

The water-swellable materials obtained from Blend Synthesis Examples 12-14 were processed on a Battenfeld BA 100 CD injection molder with nozzle temperatures between 240° F.-280° F. and the mold at room temperature. Samples from injection molding were immersed in alcohol for a minimum of 20 minutes followed by immersion in water. In each case, the material took on water and became a white, opaque, flexible hydrogel.

The concentration of water in the resultant hydrogels were determined by thermogravimetric analysis on a TA Instruments 2950 TGA instrument. For example, the hydrogel obtained using material from Blend Synthesis Example 1 was 15% solids/85% water by weight.

Mechanical performance properties for selected hydrogels were measured as ASTM D638 Type IV specimens using conventional techniques on a Model 3345 instrument from Instron Corporation. Measured values are reported in Table 1 and 2. The mechanical performance properties demonstrated that the listed hydrogels have desired mechanical properties for many applications. For example, Tables 1 and 2 list hydrogels with desired stress at peak values greater than 200 psi, while other listed hydrogels have stress at peak values greater than 500 psi.

TABLE 1

Mechanical properties for selected solution cast hydrogels (tensile).

| | Blend Synthesis Example 1 | Blend Synthesis Example 2 | Blend Synthesis Example 3 | Blend Synthesis Example 6 | Blend Synthesis Example 10 | Blend Synthesis Example 11 |
|---|---|---|---|---|---|---|
| Stress at Peak (psi) | 577.7 | 61.14 | 218.3 | 329.64 | 585 | 888.3 |
| Percent Strain at Peak | 342.2 | 172.20 | 686.7 | 591.5 | 517.16 | 2358.83 |
| Stress at Break (psi) | 553.4 | 57.0 | 218.31 | 316.0 | — | 871.26 |
| Percent Strain at Break | 345.5 | 175.8 | 686.7 | 591.5 | — | 2363.8 |
| Stress at 0.2% Yield (psi) | 385.85 | 15 | 199 | — | — | — |
| Percent Strain at 0.2% Yield | 200.11 | 11 | 670 | — | — | — |
| Young's Modulus (ksi) | 0.305 | 0.58 | .161 | 0.186 | 0.251 | 62.05 |
| Energy at Yield (lbf-in) | 19.515 | 0.174 | 34.19 | 43.80 | — | 15.11 |
| Energy at Break (lbf-in) | 64.012 | 8.37 | 37.33 | 43.80 | — | 15.43 |

TABLE 2

Mechanical properties for selected injection molded hydrogels (tensile).

| | Blend Synthesis Example 12 | Blend Synthesis Example 13 | Blend Synthesis Example 14 |
|---|---|---|---|
| Stress at Peak (psi) | 519.39 | 831.00 | 1161.98 |
| Percent Strain at Peak | 223.45 | 555.33 | 791.11 |
| Stress at Break (psi) | 497.22 | 717.06 | 1026.21 |
| Percent Strain at Break | 233.67 | 571.33 | 808.89 |
| Young's Modulus (ksi) | 711.20 | 344.92 | 354.57 |
| Energy at Yield (lbf-in) | 2.305 | 9.19 | 13.68 |
| Energy at Break (lbf-in) | 2.456 | 9.59 | 20.15 |

Irradiation can be used as a means of cross-linking the samples. Two sets of injection molded tensile specimens from Blend 14 were gamma irradiated at a dose between 26.3-34.0 kGy. The strengths of the irradiated samples are shown in Table 3.

TABLE 3

Mechanical properties for selected irradiated hydrogels (tensile).

| | Blend Synthesis Example 14 | Blend Synthesis Example 14 |
|---|---|---|
| Injection Modling Temperature, nozzle (° F.) | 255 | 260 |
| Tensile Strength (psi) | 961.70 | 1121.50 |
| Initial Elastic Modulus (psi) | 353.96 | 316.48 |
| Strain at Break (%) | 566.88 | 1337.50 |
| Toughness (%) | 3508.81 | 9837.50 |
| Water Content (%) | 45.5 | 45.0 |

Characterization

Hydrogels prepared using material from Blend Synthesis Examples 1 and 10 were tested on a MATCO load frame equipped with a standard shoulder head. The hydrogels were tested for shear under a loading of 175 lbs.

The hydrogel from Blend Synthesis 1 was tested for a simulated 1 year and 2 mm displacement, and showed no sign of shearing. Some creep was observed. The hydrogel from Blend 10 was tested for a simulated 7.5 years and a 1 mm displacement, and also showed no signs of shearing. Some creep was observed.

Rheological tests were performed on a TA Instruments AR-1000 rheometer using a parallel plate geometry and swollen hydrogel disks with a diameter of 25 mm and a thickness of 1.5 mm. All tests were performed at room temperature unless otherwise indicated. A normal force of 1-2 N was applied. First a strain sweep test was conducted to find the linear region (0.01-0.03%) and then a frequency scan (1-50Hz) was performed with a strain of 0.01%. Blend Synthesis 1 has a higher shear modulus (G*) than that of the nucleus pulposus but lower than that of the articular cartilage.

TABLE 4

Comparison of the shear viscoelastic properties between Blend Synthesis 1 and Human nucleus pulposus

| Material | Frequency (rad/s/Hz) | G* (kPa) | Tan delta (degree) |
|---|---|---|---|
| Blend Synthesis 1 | 10/1.58 | 149-340 | 5.6 |
| Nucleus pulposus | 10/1.58 | 11 | 24 |
| Articular cartilage | 10/1.58 | 600-1000 | 13 |

Crystallinity and phase separation were analyzed on a TA Instruments DSC Q1000 instrument utilizing pressure pans and a heating rate of 10° C./min. Analysis shows that the blends homogeneous with only one glass transition peak and no crystallinity peaks. After hydration, the blends show crystallinity peaks. For example, blend synthesis 1 has a Tg of 48° C. in the dry state and no apparent crystallinity peaks. In the hydrated state, Blend Synthesis 1 has a melt peak at 98° C. with an exotherm area representing 2.03% crystallinity. The melting point of 98° C. corresponds to the melting point of the polyethylene.

Use of Thermoplastic Material

The water-swellable material obtained following the procedure set forth in Blend Synthesis Example 1 was shaped and placed into an ADHESIVE TECH Model 229 Low Temp Glue Gun. The working temperature of the glue gun was 127° C. The material was extruded from the gun to a variety of substrates and environments, including onto paper, into open air, and into water (room temperature).

It was observed that the material, although extruded at a temperature over 100° C., could be handled manually without special precautions. The material cooled quickly to near room temperature.

While still hot immediately following extrusion, the material is translucent and colorless, and the shape can be modified using, for example, a spatula as a means to spread the material. The extruded material can be subsequently hydrated by contact with or immersion in water or an aqueous solution. When the material is hydrated, it gradually turns from translucent to opaque white. The development of the white color is thought to indicate the formation of crystalline regions.

Splittable Microfibers

The water-swellable material obtained from blends 12-14 spontaneously formed splittable microfibers during the extrusion process. A digital image of these microfibers is provided in FIG. 1. The strands were 2-4 mm in diameter composed of individual fibers with a diameter of 2-9 nm as determined by scanning electron microscopy. The individual fiber strands could be separated using mechanical or thermal treatments. Furthermore, the strands could be processed utilizing alcohol treatment followed by water exchange to create the hydrogel microfibers.

The invention is further set forth in the claims listed below. This invention may take on various modifications and alterations without departing from the spirit and scope thereof. In describing embodiments of the invention, specific terminology is used for the sake of clarity. The invention, however, is not intended to be limited to the specific terms so selected, and it is to be understood that each term so selected includes all technical equivalents that operate similarly.

The invention claimed is:

1. A water-swellable material comprising a non-adhesive blend of a) at least one hydrophilic polymer; and b) at least one polymer or oligomer having hydrophobic and hydrophilic recurring units, wherein the blend is effective to phase separate and is immiscible in the presence of water and wherein the blend is at least partially physically cross-linked.

2. The water-swellable material of claim 1, wherein the hydrophilic polymer comprises poly(vinyl alcohol), poly(hydroxyethyl methacrylate), poly(vinyl pyrrolidone), poly(ethyleneimine), ethoxylated poly(ethyleneimine), poly(allylamine), poly(acrylamide), poly(acrylic acid), hydrolyzed poly(acrylonitrile), or poly(glycol).

3. The water-swellable material of claim 1, wherein the polymer or oligomer having hydrophobic and hydrophilic recurring units comprises a copolymer of ethylene and vinyl alcohol, a copolymer of styrene and allyl alcohol, or diol-terminated poly(hexamethylene phthalate).

4. The water-swellable material of claim 1, wherein the blend comprises about 5%-95% by weight of poly(vinyl alcohol) and about 5%-95% by weight of the polymer or oligomer having hydrophobic and hydrophilic recurring units.

5. The water-swellable material of claim 1, wherein a majority of the hydrophilic recurring units comprise pendant hydroxy groups.

6. The water-swellable material of claim 1, wherein the polymer or oligomer having hydrophobic and hydrophilic recurring units is a copolymer having hydrophobic recurring units of the form —[$CH_2CH_2$—] and hydrophilic recurring units of the form —[$CH_2CH(OH)$—].

7. A water-swellable material comprising a non-adhesive blend of a) at least one hydrophilic polymer; b) at least one polymer or oligomer having hydrophobic and hydrophilic recurring units, and (c) a plasticizer, wherein the blend is effective to phase separate and is immiscible in the presence of water, and wherein the blend is at least partially physically cross-linked.

8. The water swellable material of claim 7, wherein the plasticizer further comprises glycerine, ethylene glycol, propylene glycol, ethanol, tetrahydrofuran, toluene, poly(ethylene glycol), dimethylformamide, dimethylacetamide, acetone, acetonitrile, cyclohexane, cyclopentane, 1,4-dioxane, ethyl acetate, glyme, methyl-tert-butyl ether, methyl ethyl ketone, pyridine, dimethylsulfoxide, or water.

9. The water-swellable material of claim 7, wherein the material is a thermoplastic having a melting temperature in the range from about 70 °–200 ° C.

10. A hydrogel in hydrated form comprising a non-adhesive, phase separated blend of polymers comprising poly (vinyl alcohol) and a polymer having hydrophobic and hydrophilic recurring units, wherein the blend is at least partially cross- linked.

11. The hydrogel of claim 10, wherein the hydrogel has a percent hydration in the range from about 10%-90%.

12. The hydrogel of claim 10, wherein the hydrogel has a percent strain at break of between 170-700.

13. The hydrogel of claim 10, wherein the hydrogel has a stress at peak value of greater than 200 psi.

14. A water-swellable material comprising a non-adhesive, physically cross-linked blend of a) at least one hydrophilic polymer; and b) at least one polymer or oligomer having hydrophobic and hydrophilic recurring units, wherein the non-adhesive, physically cross-linked blend is effective to phase separate and is immiscible in water.

* * * * *